(12) United States Patent
Riot

(10) Patent No.: US 9,689,799 B2
(45) Date of Patent: Jun. 27, 2017

(54) SYSTEM AND METHOD FOR MEASURING FLUORESCENCE OF A SAMPLE

(71) Applicant: LAWRENCE LIVERMORE NATIONAL SECURITY, LLC, Livermore, CA (US)

(72) Inventor: Vincent J. Riot, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 190 days.

(21) Appl. No.: 14/602,076

(22) Filed: Jan. 21, 2015

(65) Prior Publication Data

US 2015/0132765 A1 May 14, 2015

Related U.S. Application Data

(62) Division of application No. 13/228,361, filed on Sep. 8, 2011, now Pat. No. 8,988,684.

(51) Int. Cl.
*G01N 21/25* (2006.01)
*G01N 21/64* (2006.01)
*C12Q 1/68* (2006.01)

(52) U.S. Cl.
CPC ....... *G01N 21/6428* (2013.01); *C12Q 1/6851* (2013.01); *G01N 21/64* (2013.01); *G01N 2021/6439* (2013.01); *G01N 2201/062* (2013.01)

(58) Field of Classification Search
CPC ... C12Q 1/6851; G01N 2021/64; H04N 5/235
See application file for complete search history.

(56) References Cited

U.S. PATENT DOCUMENTS

| 3,447,479 | A | 6/1969 | Rosenberg |
| 4,365,153 | A | 12/1982 | Seigel et al. |
| 5,647,994 | A | 7/1997 | Tunnanen et al. |
| 6,099,511 | A | 8/2000 | Devos et al. |
| 6,108,611 | A | 8/2000 | McEwen |
| 6,274,869 | B1 | 8/2001 | Butler |

(Continued)

FOREIGN PATENT DOCUMENTS

KR 20120029748 A * 3/2012 ............. C12M 1/38

OTHER PUBLICATIONS

Notice of Allowance for U.S. Appl. No. 13/228,361, filed Sep. 8, 2011 in the name of Vincent J. Riot, mailed on Dec. 5, 2014.

(Continued)

*Primary Examiner* — Kara E Geisel
*Assistant Examiner* — Maurice Smith
(74) *Attorney, Agent, or Firm* — Steinfl + Bruno, LLP

(57) ABSTRACT

The present disclosure provides a system and a method for measuring fluorescence of a sample. The sample may be a polymerase-chain-reaction (PCR) array, a loop-mediated-isothermal amplification array, etc. LEDs are used to excite the sample, and a photodiode is used to collect the sample's fluorescence. An electronic offset signal is used to reduce the effects of background fluorescence and the noises from the measurement system. An integrator integrates the difference between the output of the photodiode and the electronic offset signal over a given period of time. The resulting integral is then converted into digital domain for further processing and storage.

8 Claims, 9 Drawing Sheets

(56) References Cited

U.S. PATENT DOCUMENTS

| | | | |
|---|---|---|---|
| 7,227,128 B2* | 6/2007 | Sagatelyan | G01J 1/08 250/252.1 |
| 8,808,643 B1 | 8/2014 | Benner et al. | |
| 8,988,684 B1 | 3/2015 | Riot | |
| 9,372,135 B1 | 6/2016 | Benner et al. | |
| 2002/0064880 A1 | 5/2002 | Merten et al. | |
| 2003/0148302 A1* | 8/2003 | Woo | C12Q 1/6851 435/6.16 |
| 2005/0243322 A1* | 11/2005 | Lasker | G01N 21/4795 356/432 |
| 2008/0003649 A1 | 1/2008 | Maltezos et al. | |
| 2008/0079946 A1* | 4/2008 | Greening | G01C 19/722 356/460 |
| 2009/0176314 A1 | 7/2009 | Steinboeck et al. | |
| 2009/0264319 A1 | 10/2009 | Abe et al. | |
| 2010/0045246 A1 | 2/2010 | Bryant et al. | |
| 2011/0104747 A1 | 5/2011 | Pollack et al. | |
| 2011/0224648 A1 | 9/2011 | Secci | |

OTHER PUBLICATIONS

Advisory Action issued for U.S. Appl. No. 13/228,384, filed Sep. 8, 2011 in the name of Vincent J. Riot, mailed on Mar. 12, 2014.

Non-final Office Action issued for U.S. Appl. No. 13/228,384, filed Sep. 8, 2011 in the name of Vincent J. Riot, mailed on Jul. 17, 2014.

Final Office Action issued for U.S. Appl. No. 13/228,384, filed Sep. 8, 2011 in the name of Vincent J. Riot, mailed on Jan. 16, 2015.

Non-final Office Action issued for U.S. Appl. No. 13/228,370, filed Sep. 8, 2011 in the name of W. Henry Benner, mailed on Sep. 26, 2014.

Restriction Requirement issued for U.S. Appl. No. 13/228,370, filed Sep. 8, 2011 in the name of W. Henry Benner, mailed on Jul. 2, 2014.

Notice of Allowance issued for U.S. Appl. No. 13/228,391, filed Sep. 8, 2011 in the name of W. Henry Benner, mailed on Apr. 14, 2014.

Murray, R. et al. Feedback Systems: An Introduction for Scientists and Engineers. Princeton University Press, Princeton, NJ. (2008) Chapter 10, pp. 293-314.

BacT/ALERT 3D User Manual , Jan. 2010, Healthcare Web Site, bioMerieux. 350 pages. Downloaded from the internet on Jul. 7, 2015: http://www.biomeriuex-usa.com/servlets/srt/bio/usa/dynPage?doc=USA_PRD_LST_G_PRD_USA_6.

BacT/ALERT Blood Culture Collection, Pocono Health System. 2003. 3 pages. Downloaded from the internet on Jul. 7, 2015: http://www.pmclab.org/manual/17_BacT_Blood_Culture_Collection.pdf.

MagneSil® Blood Genomic, Max Yield System, Promega, Technical Bulletin 312. Dec. 2010. Promega_MagneSilBlood_TB312. pdf. 11 pages.

Torres, C. L., et al., (Jun. 16, 2011) "LAVA: An Open-Source Approach to Designing LAMP (Loop-Mediated Isothermal Amplification) DNA Signatures" LLNL-JRNL-413646, torres_dzenitis_ LAVA_llnljrnl413646.pdf. 6 pages.

Final Office Action for U.S. Appl. No. 13/228,370, filed Sep. 8, 2011 on behalf of W. Henry Benner. Mail Date: May 19, 2015. 17 pages.

Non-Final Office Action for U.S. Appl. No. 13/228,370, filed Sep. 8, 2011 on behalf of W. Henry Benner. Mail Date: Sep. 9, 2015. 16 pages.

Notice of Allowance for U.S. Appl. No. 13/228,370, filed Sep. 8, 2011 on behalf of W. Henry Benner. Mail Date: Mar. 8, 2016. 16 pages.

Advisory Action for U.S. Appl. No. 13/228,384, filed Sep. 8, 2011 on behalf of Vincent J. Riot. Mail Date: May 6, 2015. 4 pages.

Non-Final Office Action for U.S. Appl. No. 13/228,384, filed Sep. 8, 2011 on behalf of Vincent J. Riot. Mail Date: Jun. 22, 2015. 16 pages.

Final Office Action for U.S. Appl. No. 13/228,384, filed Sep. 8, 2011 on behalf of Vincent J. Riot. Mail Date: Sep. 8, 2015. 12 pages.

* cited by examiner

SYSTEM AND METHOD FOR MEASURING FLUORESCENCE OF A SAMPLE

CROSS REFERENCE TO RELATED APPLICATIONS

This application is a divisional of U.S. patent application Ser. No. 13/228,361, filed on Sep. 8, 2011, the disclosure of which is incorporated herein by reference in its entirety. This application may also be related to U.S. Patent Application entitled "A FLUIDICS PLATFORM AND METHOD FOR SAMPLE PREPARATION" Ser. No. 13/228,370, filed on Sep. 8, 2011, to U.S. Patent Application entitled "A FLUIDICS CARTRIDGE AND REACTION PLATFORM" Ser. No. 13/228,384 filed on Sep. 8, 2011, and to U.S. Patent Application entitled "A FLUIDICS PLATFORM AND METHOD FOR SAMPLE PREPARATION AND ANALYSIS" Ser. No. 13/228,391, filed on Sep. 8, 2011 and issued as U.S. Pat. No. 8,808,643 on Aug. 19, 2014, the disclosure of all of which is incorporated herein by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to fluorescence measurement systems. In particular, it relates to a system and method for measuring fluorescence of a sample.

SUMMARY

According to a first aspect of the present disclosure, an electronic system for measuring fluorescence of a sample is provided, the electronic system comprising: a detector adapted to detect fluorescence emitted from the sample; an offset adjustment unit; and an integrator adapted to receive an output of the detector and an output of the offset adjustment unit and to provide an integrator output; wherein the output of the detector is proportional to fluorescence intensities detected by the detector, the integrator output is proportional to integration of a difference between the output of the offset adjustment unit and the output of the detector over a period of time, and the output of the offset adjustment unit is adapted to reduce effects of background fluorescence and electronic noises on the integrator output.

According to a second aspect of the present disclosure, a method for measuring fluorescence of a sample is provided, the method comprising: generating a detection output that is proportional to intensities of fluorescence emitted from the sample; generating a difference between the detection output and an offset signal; and generating a measurement output by integrating the difference over a period of time, wherein the offset signal is adapted to reduce effects of background fluorescence and electronic noises on the measurement output.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Figure 1:
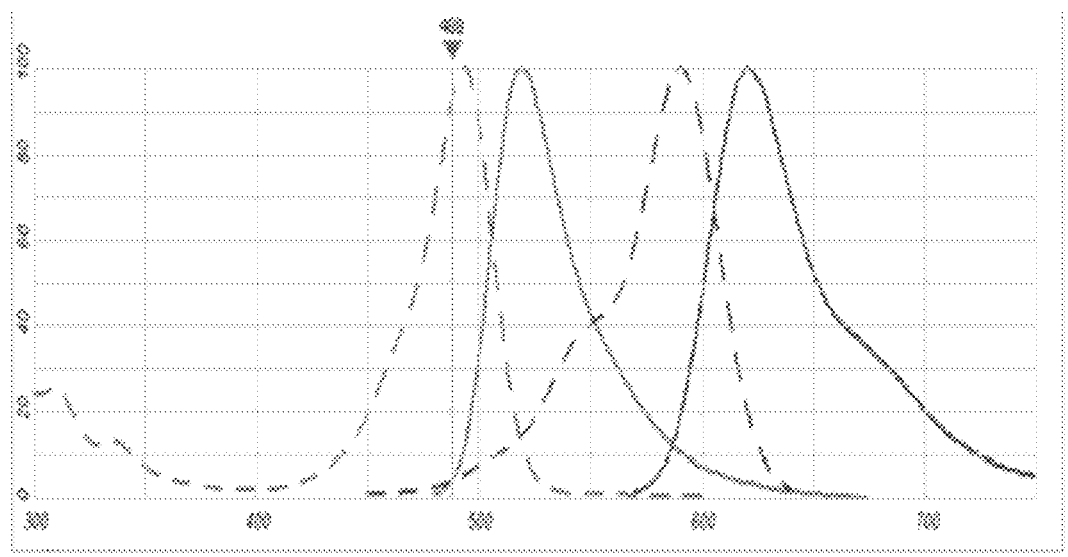
FIG. 1 depicts emission and absorption spectra of two fluorescent dyes.

Fluorescence is the emission of light by a substance (e.g. a fluorescent dye) that has absorbed light or other electromagnetic radiation of a different wavelength. FIG. 1 shows the emission and absorption spectra of two fluorescent dyes.

Fluorescence detection has been used to determine the presence or absence of target DNA sequences or other fluorescence-dye-labeled materials. However, the background fluorescence and the noises from the detection system may compromise the detection system's sensitivity, detection limits and signal-to-noise ratio. To improve signal-to-noise ratios and the other parameters, some fluorescence detection systems use optical filters and lenses in order to reduce the effects of noises and background fluorescence.

This application discloses a system and method that improves fluorescence signal-to-noise ratios through adaptive electronic offset compensation. According to one embodiment of the present disclosure, optical filters or lenses are not necessary for normal operations. But the use of optical filters and lenses may further improve the system's performance.

Figure 2:
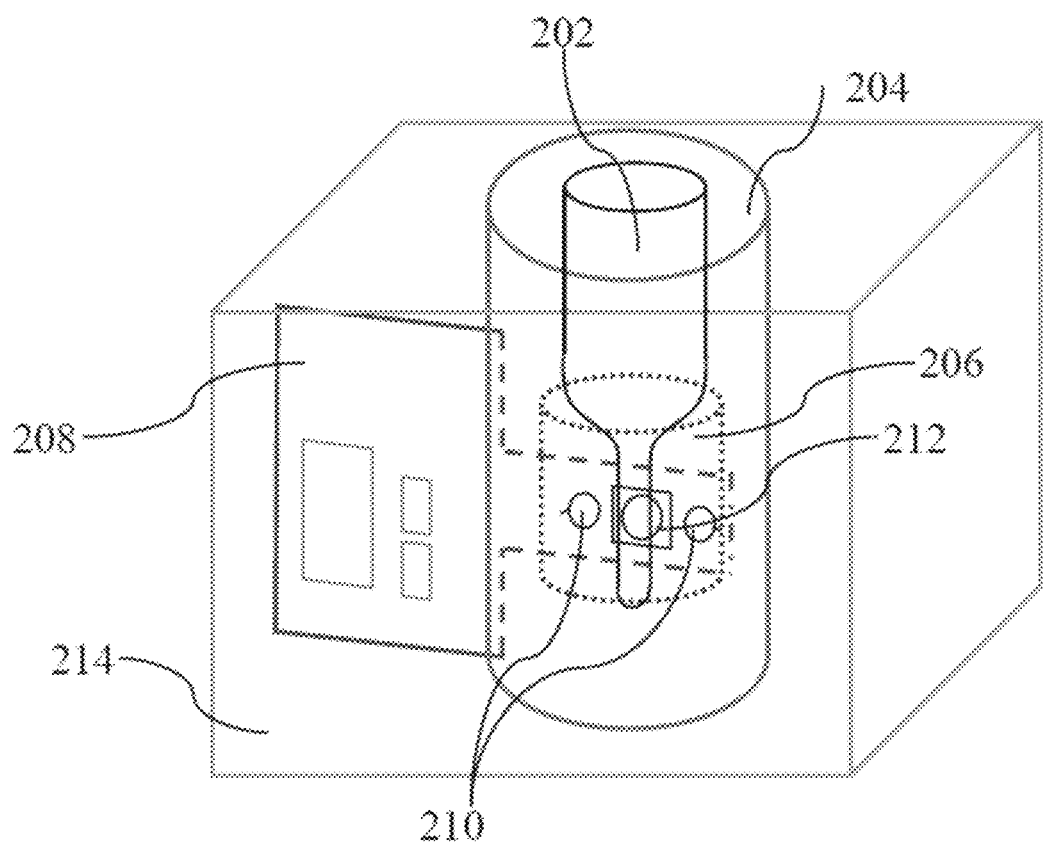
FIG. 2 depicts a mechanical setup of the measurement system, according to one embodiment of the present disclosure.

FIG. 2 shows a mechanical setup of the measurement system, according to one embodiment of the present disclosure. A vial (202) containing the measured sample is inserted into the cavity formed by insulation foam (204). Inside the insulation cavity is a heater (206) for maintaining the vial at a constant temperature. For example, the reaction temperature must be maintained at 60° C. for a loop-mediated isothermal amplification (LAMP) array. A printed circuit board (PCB) (208) is so placed that the LEDs (210) and the photodiodes (212) on the PCB (208) are closed enough to the vial (206) to receive detectable fluorescence emissions.

In a further embodiment, the PCB (208) is so placed that the vial (202) is within 0.5 mm from the photodiode (212) and the LEDs (210) are in contact with the vial (202). The vial (202), the insulation foam (204), the heater (206) and the PCB (208) are all located in an enclosure (214).

In a further embodiment, the measurement system is turned on and off manually. In another embodiment, the measurement system is turned on automatically when the vial (202) is inserted into the insulation cavity.

Figure 3:
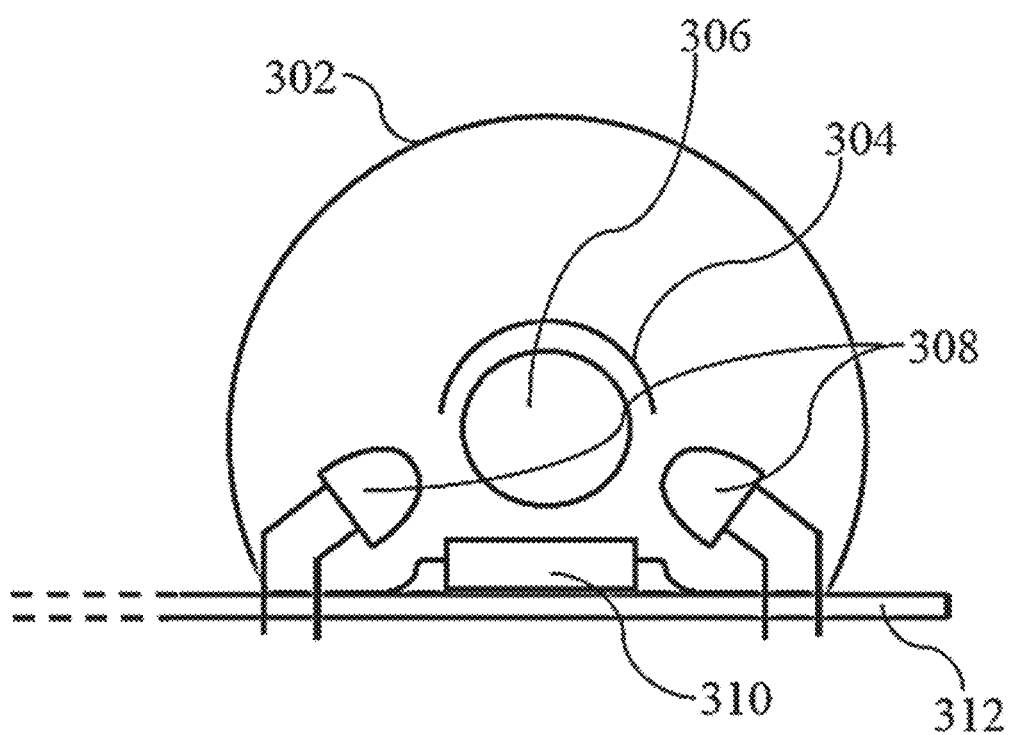
FIG. 3 depicts a cross-sectional view of the mechanical setup of the measurement system, according to one embodiment of the present disclosure

FIG. 3 shows a cross-sectional view of the mechanical setup of the measurement system, according to one embodiment of the present disclosure. The vial (306) is located on the top of the photodiode (310) and is surrounded by the LEDs (308). The vial (306), the photodiode (310) and the LEDs (308) are so arranged to ensure the satisfactory excitation and detection results. In a further embodiment, the vial (306) is within 0.5 mm from the photodiode (310) and the LEDs (308) are in contact with the vial (306). The heater (304) is located closed to the vial to ensure efficient heating, and the insulation foam (302) covers the vial (306) and the heater (304) to ensure good thermal insulation.

In a further embodiment, the LEDs (308) are through-hole components fixed on the PCB (312). In another embodiment, the photodiode (310) is surface-mounted on the PCB (312).

According to one embodiment of the present disclosure, a vial (306) loaded with the measured sample is inserted into the insulation cavity. After the vial (306) is inserted, the measurement system is turned on (either automatically or manually). The heater (304) starts heating the vial (306) and the measurement system controls and maintains the temperature of the measured sample at a given level. The measurement system then lights up the LEDs (308) that emit electromagnetic waves exciting the measured sample (or the fluorescence dye in the measured sample) contained in the vial (306). The photodiode (310) then picks up the fluorescence emitted from the measured sample for further processing.

According to one embodiment of the present disclosure, the measurement system is used for loop-mediated isothermal amplification (LAMP) assays. This measurement system can also be used for other assays that use fluorescence detection, such as polymerase chain reaction (PCR) assays and real-time polymerase chain reaction (RT-PCR) assays.

Figure 4:
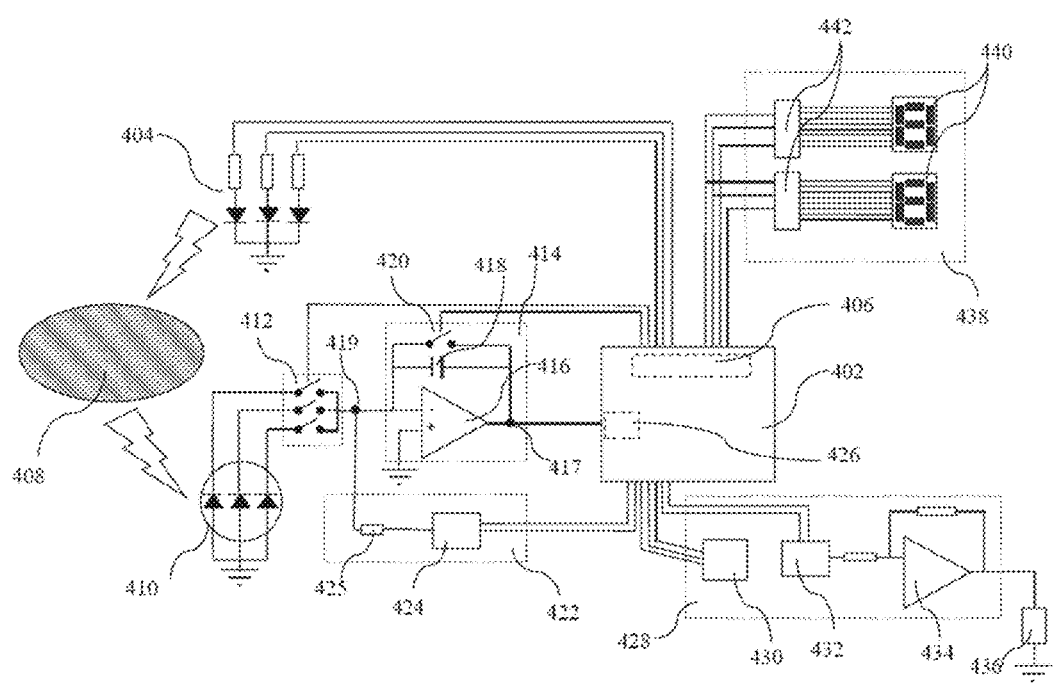
FIG. 4 depicts an exemplary circuitry of the measurement system, according to one embodiment of the present disclosure.

FIG. 4 shows an exemplary circuitry of the measurement system, according to one embodiment of the present disclosure. According to an embodiment of the present disclosure, a microcontroller (402) controls and drives one or more LEDs (404). The microcontroller (402), through its general I/O (406), selects and drives one of the LEDs (404). When turned on, the selected LED (404) emits electromagnetic waves of wavelengths that fall within the fluorescence excitation ranges of the measured sample (408) or fluorescence dyes in the measured sample (408). Some materials have auto-fluorescence and emit fluorescence without external excitation. For a sample containing such a material, the measurement system may directly measure the fluorescence emissions from the sample without first turning on the LED (404). In another embodiment, other light sources such as laser diodes, etc., may be used in place of the LED (404), so long as the source is capable of invoking fluorescence responses of the measured sample (408) or fluorescence dyes in the measured sample (408).

According to one embodiment of the present disclosure, the measurement system collects fluorescence from the measured sample (408) using a photodiode (410). The photodiode (410) has a detection wavelength range that encompasses or overlaps the wavelength range of the fluorescence emissions from the measured sample (408). According to another embodiment of the present disclosure, the measurement system uses an array of photodiodes (410) that have different detection wavelength ranges. The microcontroller (402) selects the output of one of the photodiodes (410) through a multiplexer (412). This allows the measurement system to detect fluorescence emissions at different wavelengths. In another embodiment of the present disclosure, the multiplexer can disconnect the photodiode (410) from the integrator (414) while the integrator (414) is being reset. In another embodiment, other types of detectors, such as photomultiplier tubes, charge-coupled devices (CCD), etc., may be used, so long as the detector is capable of detecting fluorescence emissions of the measured sample (408).

According to one embodiment of the present disclosure, the integrator (414) receives as inputs the output of the photodiode (410) and the output of the offset adjustment unit (422). The integrator (414) integrates over a period of time the difference between the output of the photodiode (410) and the output of the offset adjustment unit (422). The integrator (414) outputs the resulting integral.

In a further embodiment, the integrator (414) comprises a trans-impedance amplifier. In another embodiment, the trans-impedance amplifier comprises an operational amplifier (416) and a capacitor (420). In another embodiment, the integrator (414) further comprises a reset switch (420), through which the microcontroller (402) resets the integrator (414). The reset switch (420) is connected to the capacitor (418) in parallel. Closing the reset switch (420) makes the capacitor (418) short-circuited and thus zeros the charges stored in the capacitor (418). As a result, the integrator (414) is reset.

According to one embodiment of the present disclosure, the offset adjustment unit (422) comprises a digital-to-analog converter (offset-DAC) (424). The offset-DAC (424) converts the offset control signal from the microcontroller (402) into analog offset signal (voltage or current). The analog offset signal is then output to the integrator (414). In a further embodiment, before being sent to the integrator (414), the analog offset signal may go through amplification, voltage-to-current conversion, current-to-voltage conversion, or other analog processing. In a further embodiment, the offset adjustment unit (422) further comprises a resistor (425) that is connected to the input of the integrator (414) and to the output of the offset-DAC (424). This resistor accommodates and allows for any voltage difference between the input of the integrator (414) and the output of the offset-DAC (424).

According to one embodiment of the present disclosure, the analog-to-digital converter (ADC) (426) digitizes the output of the integrator (414) for further processing and storage. The ADC (426) may be an external discrete component or a built-in unit of the microcontroller (402).

According to one embodiment of the present disclosure, the measurement system further comprises a temperature controller (428). The temperature controller (428) maintains the temperature of the measured sample (408) at a given level during measurement. The temperature controller comprises a temperature sensor (430), a digital-to-analog converter (temp-DAC) (432), and a power amplifier (434). The temperature sensor (430) reads the temperature of the measured sample (408). The microcontroller (402) receives the temperature reading from the temperature sensor (430), processes the temperature readings, and outputs a heater control signal. The temp-DAC (432) analogizes the heater control signal; and the power amplifier (434) amplifies the analog heater control signal. The heater (436) heats the measured sample (408) according to the amplified analog heater control signal. In a further embodiment, the heater control signal determines the amount of current going through the heater (436). The temperature control mechanism may be implemented according to common feedback control algorithms, e.g., the PID control algorithm.

According to one embodiment of the present disclosure, the measurement system further comprises a digital display (438) for displaying the current temperature of the measured sample (408), the output of the integrator (414), etc. In a further embodiment, the digital display comprises at least one 7-segment LED display (440). In another embodiment, the digital display (438) further comprises at least one interface circuit (442) that interfaces between the 7-segment LED display (440) and the microcontroller (402).

According to one embodiment of the present disclosure, the photodiode (410) of FIG. 4 outputs a current, $i_p(t)$ in response to the fluorescence collected by the photodiode (410). The current $i_p(t)$ flows out of the node 419, through the multiplexer (412) and the photodiode (410), then to the ground. $i_p(t)$ comprises two components: 1) the current in response to the fluorescence caused by the reactions that are taking place in the measured sample, $i_s(t)$, and 2) the current resulting from the background fluorescence and the noises in the measurement system, $i_n(t)$. Therefore, $$i_p(t) = i_s(t) + i_n(t)$$

Assuming that the output of the offset adjustment unit (422) is $i_{offset}(t)$, the total current flowing through the capacitor will be $$i_C(t) = i_p(t) - i_{offset}(t)$$

$$i_C(t) = i_s(t) + i_n(t) - i_{offset}(t),$$

where the current $i_C(t)$ follows from the node 417 through the capacitor (418) to the node 419 of FIG. 4, and the current $i_{offset}(t)$ flows from the offset adjustment unit (422) into the node 419 of FIG. 4.

Assuming the capacitor (418) of the integrator has capacitance, C, and the integration time is T, then the output of the integrator (414), $V_{int}(t)$, at node 417 will be $$V_{int}(t) = \frac{1}{C} \int_T (i_p(t) - i_{offset}(t)) dt$$

$$= \frac{1}{C} \int_T (i_s(t) + i_n(t) - i_{offset}(t)) dt$$

$$= \frac{1}{C} \int_T (i_s(t) + i_n(t) - i_{offset}(t)) dt$$

$$= \frac{1}{C} \int_T i_s(t) dt + \frac{1}{C} \int_T i_n(t) dt - \frac{1}{C} \int_T i_{offset}(t) dt$$

Thus, $V_{int}(t)$ comprises three components: 1) the reaction output, $V_{reaction}(t)$; 2) the noise output, $V_{noise}(t)$; and 3) the offset output, $V_{offset}(t)$, where $$V_{reaction}(t) = \frac{1}{C} \int_T i_s(t) dt$$

$$V_{noise}(t) = \frac{1}{C} \int_T i_n(t) dt$$

$$V_{offset}(t) = \frac{1}{C} \int_T i_{offset}(t) dt$$

$$V_{int}(t) = V_{reaction}(t) + V_{noise}(t) - V_{offset}(t)$$

Figure 5:
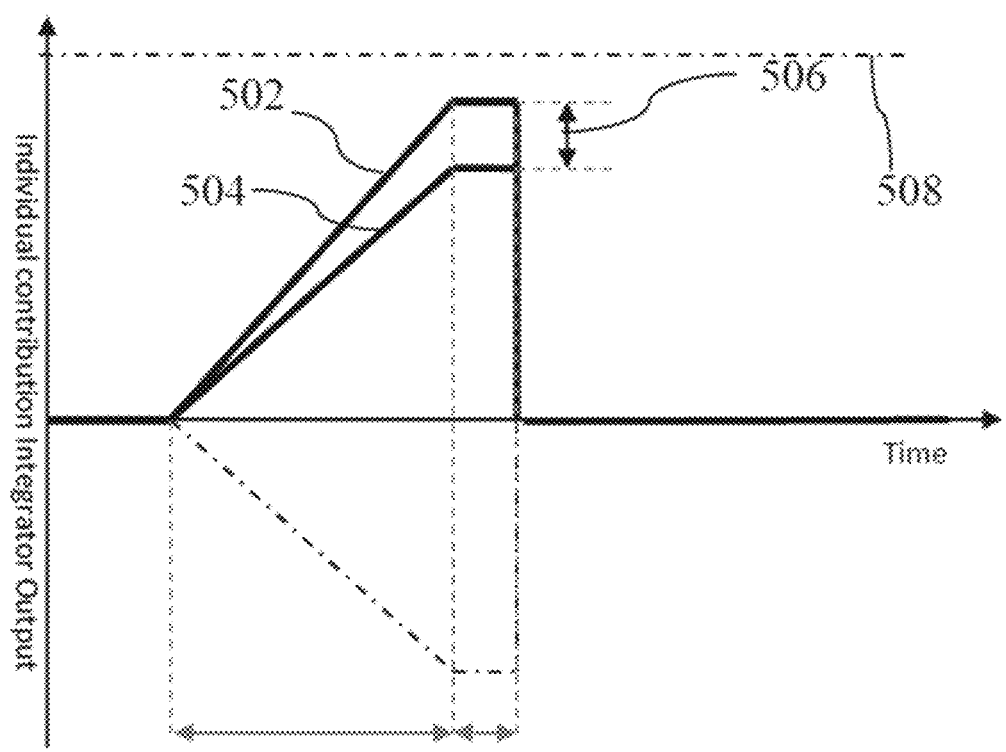
FIG. 5 depicts integrator outputs for two different samples when there is no offset adjustment, according to one embodiment of the present disclosure.

FIG. 5 shows integrator outputs for two different samples when there is no offset adjustment (i.e., $i_{offset}(t) = 0$ and $V_{offset} = 0$). Curve 502 represents the integrator output for a reactive sample, and therefore, Curve 502 can be expressed as follows:

$$V_{int,502}(t) = \frac{1}{C} \int_T (i_s(t) + i_n(t)) dt = V_{reaction}(t) + V_{noise}(t).$$

Curve 504 represents the integrator output for a nonreactive sample (no reaction), and therefore, Curve 504 can be expressed as follows:

$$V_{int,504}(t) = \frac{1}{C} \int_T (i_n(t)) dt = V_{noise}(t).$$

As can be seen from FIG. 5 and the expression above, $V_{int,504}(t)$ is non-zero because of the presence of background fluorescence and the noises from the measurement system. Sometimes, the background fluorescence and the noises are so strong that the difference (506) between $V_{int,502}(t)$ and $V_{int,504}(t)$ is too small to tell whether the reactions have taken place in the measured sample. In addition, large $V_{noise}(t)$ makes $V_{int,502}(t)$ close to the limit (508) of the ADC (426) of FIG. 4. This makes it difficult to further amplify $V_{int,502}(t)$ and to detect large $V_{reaction}(t)$.

According to one embodiment of the present disclosure, the measurement system reduces the effects of the background fluorescence and the noises from the measurement system by adaptively adjusting the output of the offset adjustment unit (422) of FIG. 4, $i_{offset}(t)$ (and thus $V_{offset}(t)$).

Figure 6:
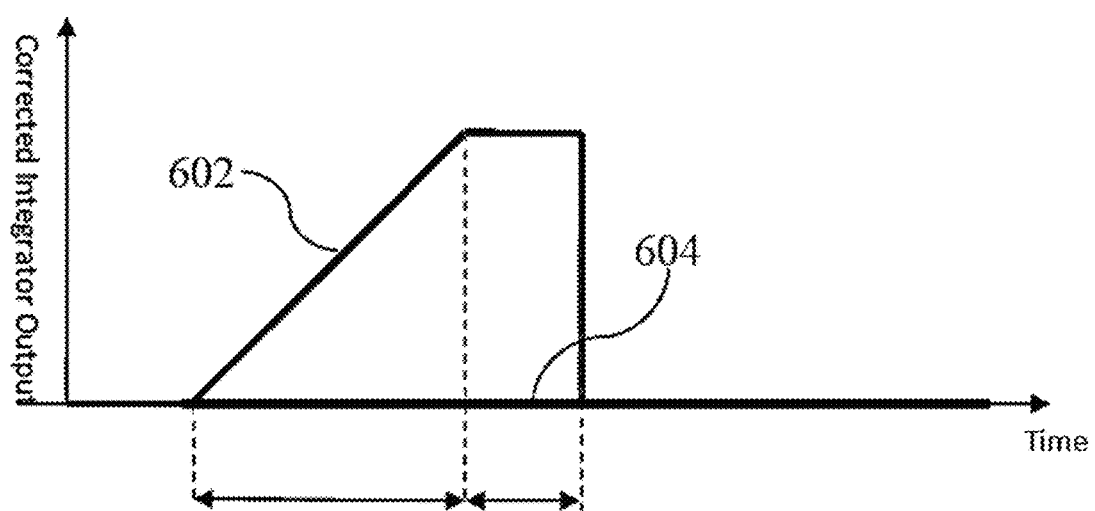
FIG. 6 depicts integrator output curves in an ideal case where $i_{offset}(t)$ is the same as $i_n(t)$, according to one embodiment of the present disclosure.

FIG. 6 shows integrator output curves in an ideal case where $i_{offset}(t)$ is the same as $i_n(t)$ (and thus $V_{offset}(t) = V_{noise}(t)$). In this ideal case, the integrator output (604) for a nonreactive sample is zero. The integrator output (602) for a reactive sample comes from the reactions in the sample. Because $V_{noise}(t)$ is fully cancelled by $V_{offset}(t)$, it is easy to detect, amplify and further process the integrator output (602) for a reactive sample. It is also easy to tell whether the reactions have taken place in the measured sample.

Figure 7:
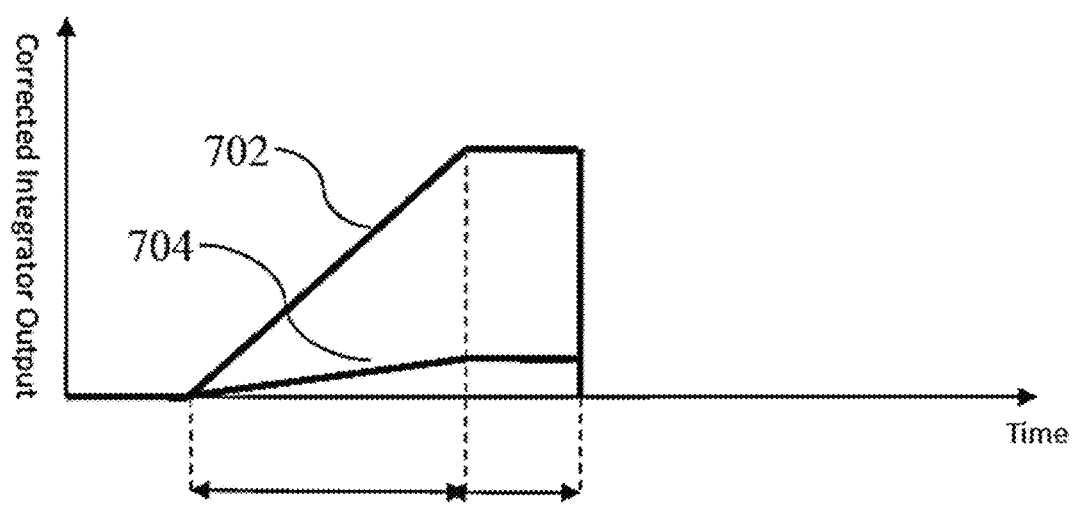
FIG. 7 depicts integrator output curves in a non-ideal case where $i_{offset}(t)$ closely traces $i_n(t)$, but is not identical to $i_n(t)$, according to one embodiment of the present disclosure.

FIG. 7 shows integrator output curves in a non-ideal case where $i_{offset}(t)$ closely traces $i_n(t)$, but is not identical to $i_n(t)$. Because $i_{offset}(t)$ is not identical to $i_n(t)$, the integrator output (704) for a nonreactive sample is nonzero. However, the integrator output (704) for a nonreactive sample is much smaller compared to that of FIG. 5. The small ($V_{noise}(t) - V_{offset}(t)$) makes it easy to detect, amplify and further process the integrator output (702) for a reactive sample. It is also easy to tell whether the reactions have taken place in the measured sample.

According to one embodiment of the present disclosure, the output of the offset adjustment unit (422) of FIG. 4 is a constant. The microcontroller (402) sets the constant according to a user's input. The constant should be so selected that it is easy to distinguish the integrator output for a reactive sample from that for a nonreactive sample.

In a further embodiment, the reaction in the measured sample (408) has already completed. In this embodiment, the microcontroller (402) first turns off the LED (404) of FIG. 4. The microcontroller (402) automatically adjusts the output of the offset adjustment unit (422) until reaching a background offset value that makes the output of integrator (414) zero. Then, the microcontroller sets the output of the offset adjustment unit (422) to be the background offset value, turns on the LED (404), and starts measuring the fluorescence emissions of the sample as stated above. The output of the offset adjustment unit (422) is maintained to be the background offset value until the measurement is completed.

In another further embodiment, the reaction in the measured sample (408) is to be monitored in real time. In this embodiment, the microcontroller first turns on the LED (404), raises the temperature of the measured sample (408) to a target reaction temperature, and starts measuring the fluorescence emissions of the measured sample (408). At the same time, the microcontroller (402) automatically adjusts the output of the offset adjustment unit (422) to make the output of integrator (414) zero or close to zero. This adjustment process continues until before the reaction in the measured sample (408) starts (e.g., 3 minutes before the reaction starts). Then, the microcontroller (402) sets the output of the offset adjustment unit (422) to be the offset value found at the end of the adjustment process and continues measuring fluorescence emissions of the measured sample (408). The output of the offset adjustment unit (422) is maintained, throughout the measurement, at the offset value found at the end of the adjustment process. Because the offset value is found when the measured sample is maintained at a target reaction temperature, the offset value reduces the effects of temperature dependencies of background fluorescence, electronic noises, the photodiode (410) and the LED (404).

Figure 8:
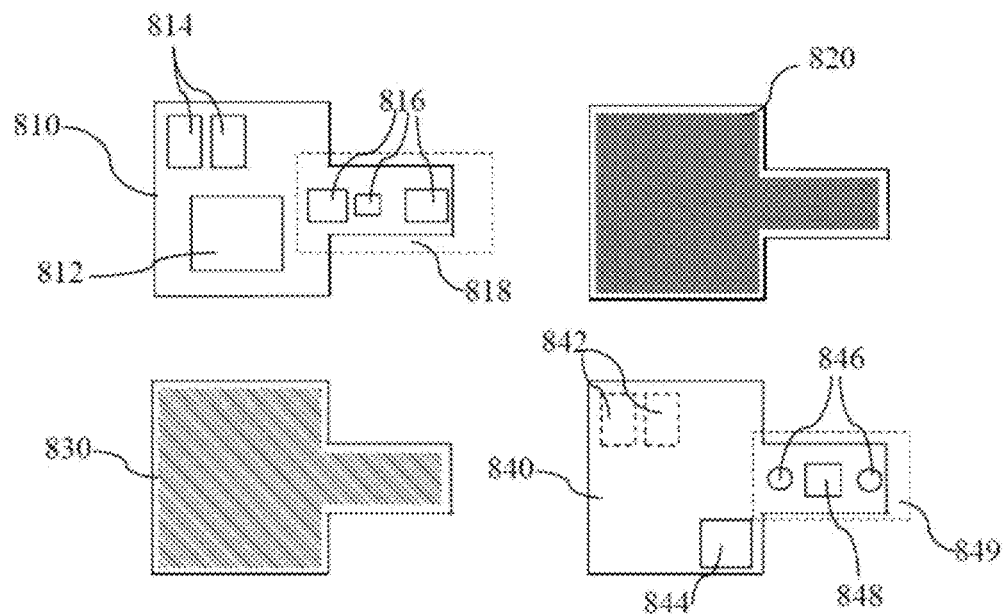
FIG. 8 depicts printed circuit board layouts for the measurement system, according to one embodiment of the present disclosure.

FIG. 8 shows a printed circuit board (PCB) layouts for the measurement system, according to one embodiment of the present disclosure. Layout 810 represents the layout of the top layer of the PCB, which comprises the footprint area (812) for the microcontroller, the footprint area (814) for the seven-segment display(s), and the footprint area (816) for the multiplexer, switches, and pre-amplifiers. Layout 820 represents the layout for the ground layer of the PCB. Layout 830 represents the layout for the power layer of the PCB. Layout 840 represents the bottom layer of the PCB, which comprises the footprint area (842) for the shift registers, the footprint area (844) for the power amplifier; the footprint area (846) for the LEDs, and the footprint area (848) for the photodiode. In a further embodiment, the connection traces are so routed that area 849 of the bottom layer (840) contains no connection trace. Connection traces necessary for the LEDs and the photodiode should be placed in area 818 of the top layer (810).

Figure 9:
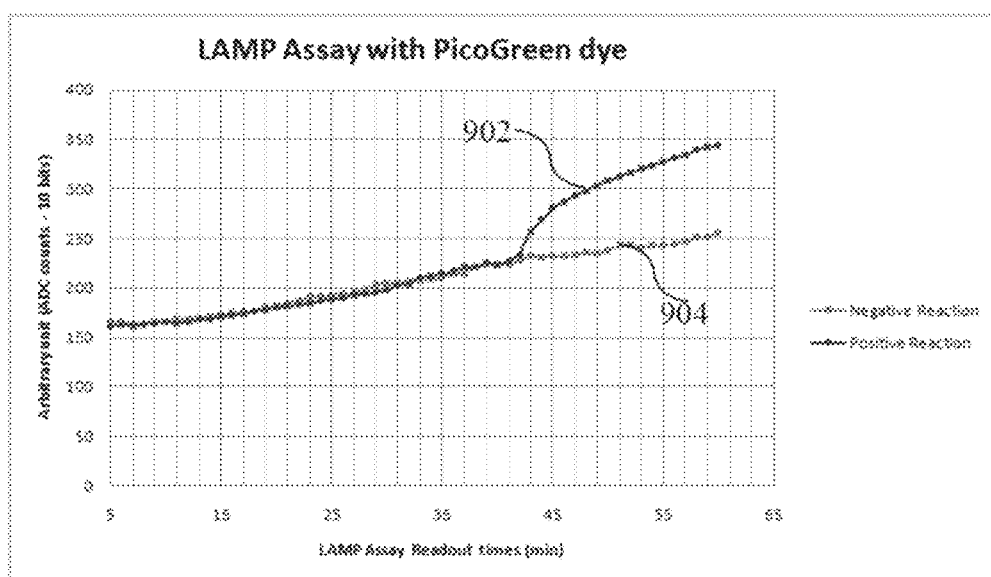
FIG. 9 depicts integrator output curves for two LAMP assays with Pico Green, according to one embodiment of the present disclosure

FIG. 9 shows integrator output curves for two LAMP assays with Pico Green, according to one embodiment of the present disclosure. As shown in FIG. 9, the reactive sample produces a clearly different integrator output curve (902) from that (904) of a nonreactive sample. These curves were obtained without using any optical components beyond LEDs and photodiodes.

The examples set forth above are provided to give those of ordinary skill in the art a complete disclosure and description of how to make and use the embodiments of the system and method for measuring fluorescence of a sample of the disclosure, and are not intended to limit the scope of what the inventor regards as his disclosure. Modifications of the above-described modes for carrying out the disclosure can be used by persons of skill in the art, and are intended to be within the scope of the following claims.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications can be made without departing from the spirit and scope of the present disclosure. Accordingly, other embodiments are within the scope of the following claims.

LIST OF REFERENCES

1. Rapid and Simple Method for Purification of Nucleic Acids. Boom, R. et al. J. Clin. Microbial. 1989 28:495-503.
2. Process for Isolating Nucleic Acid. Boom, Adriannse, Kievits, Lens, 1993 U.S. Pat. No. 5,234,809.
3. Rapid isolation of genomic DNA from whole blood to borosilicate particles. Bush, C. and M. Harvey, 1991 Clin. Chem. 37:1060.
4. SmartCycler System Brochure, Cepheid http://www.cepheid.com/media/files/brochures/SC Brochure.pdf
5. Bio-Seeq PLUS brochure, Smiths Detection http://www-.smithsdetection.com/eng/Bio-Seeq PLUS.php
6. An integrated portable hand-held analyser for real-time isothermal nucleic acid amplification, M. C. Smith et al. Analytica Chimica Acta, 2007 598: 286-294
7. SeptiFast Brochure, Roche http://molecular.roche.com/commonfiles/media/pdf/51septifast.pdf
8. GeneXpert System Brochure 0112-04, Cepheid http://www.cepheid.com/media/files/brochures/GeneXpert%20Brochure 0112-04.pdf
9. Bio-Seeq Product Summary, Smiths Detection http://www.smithsdetection.com/media/Bioseeq_Ciinical_product_summary021809.pdf
10. Maxwell 16 DNA Purification Kits, Promega Technical Manual 284 Promega_Maxwell_TM284.pdf

What is claimed is:
1. A method for measuring fluorescence of a sample, comprising
providing an excitation source configured to irradiate the sample with electromagnetic waves that induce the sample's fluorescence emissions;

providing a detector comprising an integrator circuit and configured to detect fluorescence emitted from the sample;

irradiating, with the excitation source, the sample with electromagnetic waves of wavelengths that that induce the sample's fluorescence emissions;

generating, by the detector, a detection output signal that is proportional to intensities of fluorescence emitted from the sample;

generating, by the detector, a difference between the detection output signal and an offset signal; and generating, by the integrator circuit, a measurement output signal by integrating the difference over a period of time, wherein
the offset signal is adjusted to reduce effects of background fluorescence and electronic noises on the measurement output signal.

2. The method of claim 1,
wherein the irradiation is performed using a light-emitting diode.

3. The method of claim 1, further comprising maintaining the sample at a given temperature.

4. The method of claim 1, further comprising maintaining the sample at a given temperature according to a proportional integral derivative (PID) control algorithm.

5. The method of claim 1, wherein the offset signal is a constant.

6. The method of claim 1, wherein the offset signal is a constant such that
the measurement output signal is zero or close to zero when no electromagnetic wave from the excitation source is irradiated on the sample.

7. The method of claim 1, wherein the offset signal is a constant such that
the measurement output signal is zero or close to zero before any reaction takes place in the sample.

8. The method of claim 1, wherein the generation of the detection output signal is carried out using a photodiode, a charge-coupled device, or a photomultiplier tube.

* * * * *